(12) United States Patent
Ein-Gal

(10) Patent No.: US 7,945,023 B2
(45) Date of Patent: May 17, 2011

(54) STEREOTACTIC RADIOTHERAPY WITH ROTATING ATTENUATOR

(76) Inventor: Moshe Ein-Gal, Ramat Hasharon (IL)

(*) Notice: Subject to any disclaimer, the term of this patent is extended or adjusted under 35 U.S.C. 154(b) by 0 days.

(21) Appl. No.: 12/420,066

(22) Filed: Apr. 8, 2009

(65) Prior Publication Data

US 2010/0260319 A1 Oct. 14, 2010

(51) Int. Cl.
*A61N 5/10* (2006.01)

(52) U.S. Cl. .......................................... 378/65; 378/153

(58) Field of Classification Search .................... 378/65, 378/145–153

See application file for complete search history.

(56) References Cited

U.S. PATENT DOCUMENTS

2006/0193441 A1* 8/2006 Cadman .................. 378/153

* cited by examiner

*Primary Examiner* — Hoon Song

(74) *Attorney, Agent, or Firm* — Dekel Patent Ltd.; David Klein

(57) ABSTRACT

A radiotherapy system including a radiation source operable to produce a radiation beam towards a target, an orientation changer operable to change a relative position of the radiation source with respect to the target, and a multileaf attenuator including attenuating leaves including respective spatially varying attenuation properties and a positioner in communication with the orientation changer, each of the attenuating leaves having a leaf length, leaf thickness, leaf center and leaf direction, wherein the leaf direction is a line intersecting the leaf center along the leaf thickness, wherein the radiation beam includes one or more beam segments, wherein a beam segment is the part of the beam intercepted by one of the attenuating leaves, and wherein the target includes one or more target segments, wherein a target segment is that part of the target that intercepts a corresponding one of the beam segments, wherein each of the attenuating leaves is operative to modulate an intensity of a corresponding beam segment by selective attenuation of the leaf thickness along the leaf length, and wherein the positioner is operable to vary at least one of a leaf center position and a leaf direction relative to the radiation source in accordance with positions of the corresponding target segment and the radiation source.

3 Claims, 11 Drawing Sheets

STEREOTACTIC RADIOTHERAPY WITH ROTATING ATTENUATOR

FIELD OF THE INVENTION

The present invention relates generally to stereotactic radiotherapy with radiation protection, and particularly to a system and method for stereotactic radiotherapy with a rotating attenuator.

BACKGROUND OF THE INVENTION

Medical equipment for radiation therapy treats tumorous tissue with high energy radiation. The dose and the placement of the dose must be accurately controlled to insure both that the tumor receives sufficient radiation to be destroyed, and that damage to the surrounding and adjacent non-tumorous tissue, referred to as organs at risk (OAR), is minimized.

Radiation therapy typically uses a radiation source that is external to the patient, typically either a radioisotope, such as cobalt-60, or a high energy x-ray source, such as a linear accelerator. The external source produces a collimated beam directed into the patient to the tumor site. However, external-source radiation therapy undesirably irradiates a significant volume of OAR in the path of the radiation beam along with the tumorous tissue. The adverse effect of irradiation of healthy tissue may be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also may be reduced by tightly collimating the radiation beam to the general cross section of the tumor taken perpendicular to the axis of the radiation beam. Numerous systems exist for producing such a circumferential collimation, such as systems with multileaf collimators. The multileaf collimator (MLC) may control the width and offset of the radiation beam as a function of gantry angle so that tumorous tissue may be accurately targeted.

Collimation is just one way of modulating the radiation beam. Additionally or alternatively, the radiation beam may be attenuated. Collimators control the outline of the radiation beam; attenuators control the intensity of the radiation beams that are beamed at the tissue. Phrased more technically, collimators block radiation so as to create a generally binary spatial intensity distribution, while attenuators typically produce continuous spatial modulation of the beam intensity by selective attenuation.

For example, Intensity Modulated Radiotherapy (IMRT) is aimed at irradiating a target while protecting healthy tissue, especially organs-at-risk (OAR). Intensity modulation is implemented either by multileaf collimators or by attenuating modulators. A desired intensity map is approximated by segmentation: forming a sequence of aperture segments consecutively shaped by an MLC.

The apertures (and associated respective intensities) may be modified continuously during irradiation, producing what is generally called Dynamic IMRT. Dynamic modulation is possible by continuous irradiation while changing the orientations and/or the apertures together with the respectively associated intensities.

A single arc IMRT has been described. The procedure involves rotating the beam about the target for an arc of one or two revolutions, while MLC-apertures and associated intensities are continuously modified. Although the rotational speed is low—about one revolution per minute—modulation performance is limited by the short time-interval allocated for each orientation increment.

A theoretical approach applicable to a single arc IMRT has been described by Brahme et al: "Solution of an integral equation encountered in rotation therapy", Phys. Med. Biol., 27, (1982), No. 10, 1211-1229. An analytical expression is presented for the parallel beam profile in each orientation for obtaining uniform target dose while protecting a central organ, whereas the target and the organ are concentric circles. Extension of the expression to non-concentric circles was observed by Bortfeld et al: "Single-Arc IMRT?", Phys. Med. Biol., 54, (2009) N9-N20. Beam modulation may be implemented by a "sliding window" MLC technique whereby continuous exposure time is spatially controlled.

IMRT can also be implemented by compensators, also referred to as attenuating modulators. A compensator uses a two-dimensional attenuating pattern that modulates the beam intensity by spatially-selective attenuation. An example of this is described in "Compensators: An alternative IMRT delivery technique", Sha X. Chang et al, Journal of applied Clinical Medical Physics, Vol 5, No. 3 (2004).

IMRT via 2D attenuating modulators obviates segmentation. Attenuating modulators are fabricated respectively for each of the 5-7 orientations selected for the treatment. A respective attenuating modulator is placed in position prior to each oriented irradiation. A single-arc IMRT using 2D attenuating modulators would be prohibitively expensive, since a large set of modulators would have to be fabricated for each patient and it is complicated to replace/move them at high speed.

SUMMARY OF THE INVENTION

The present invention seeks to provide a system and method for stereotactic radiotherapy with a rotating attenuator, as is described more in detail hereinbelow. Intensity modulation of beam segments is carried out by corresponding attenuators whose position is individually controlled according to the radiation orientation.

The invention relates to a device for intensity modulation of beam segments by corresponding attenuators whose position is individually controlled according to the radiation orientation. The invention makes use of the following geometrical observation: when a radius vector (originating at an origin) follows a trajectory in space, the scaled version of the radius vector follows a scaled trajectory, e.g., when the trajectory is a circle having a rotational radius about a center, then the scaled trajectory is a scaled circle having a parallel scaled rotational radius. Consequently, a beam oriented toward an object whose location is represented by a radius vector originating at a radiation source can be attenuated by an attenuator located at a point on the scaled vector such that the scaling factor is smaller than one. The attenuator thickness along the radius vector and the attenuator material determine the attenuation properties.

There is thus provided in accordance with an embodiment of the present invention, for use with a radiotherapy system including a radiation source operable to produce a radiation beam towards a target, and an orientation changer operable to change a relative position of the radiation source with respect to the target, a multileaf attenuator including:

attenuating leaves including respective spatially varying attenuation properties and a positioner in communication with the orientation changer, each of the attenuating leaves having a leaf length, leaf thickness, leaf center and leaf direction, wherein the leaf direction is a line intersecting the leaf center along the leaf thickness, wherein the radiation beam includes one or more beam segments, wherein a beam segment is the part of the beam intercepted by one of the attenuating leaves, and wherein the target includes one or more target segments, wherein a target segment is that part of the target that intercepts a corresponding one of the beam segments, wherein each of the attenuating leaves is operative to modulate an intensity of a corresponding beam segment by selective attenuation of the leaf thickness along the leaf length, and wherein the positioner is operable to vary at least one of a leaf center position and a leaf direction relative to the radiation source in accordance with positions of the corresponding target segment and the radiation source.

In accordance with an embodiment of the present invention the radiation beam is directed towards an organ incorporating organ segments, wherein an organ segment is part of the organ intercepting a corresponding beam segment, the organ segment having an organ segment center, and wherein the positioner is operable to position each of the attenuating leaves such that distances from centers of the leaves and the corresponding centers of the organ segments to the radiation source are related by a scaling factor.

In accordance with an embodiment of the present invention the leaf direction generally intersects the radiation source and the corresponding organ segment center.

In accordance with an embodiment of the present invention the orientation changer is operable to rotate the target about a target rotational axis and the leaf direction is generally parallel to the shortest line intersecting the radiation source and the target rotational axis.

In accordance with an embodiment of the present invention the positioner is operable to position any of the attenuating leaves by positioning two leaf portions.

In accordance with an embodiment of the present invention the orientation changer is operable to rotate the target about a target rotational axis, the positioner includes positioner rotational axes parallel to the target rotational axis, and the positioner is operable to position two leaf portions on respective common-radius circular trajectories about respective positioner rotational axes parallel to the target rotational axis.

In accordance with an embodiment of the present invention the radiation source is stationary, the radiation beam is generally horizontal and the target rotational axis is generally vertical.

In accordance with an embodiment of the present invention, for each attenuation leaf, an attenuation pattern is symmetrical about the leaf center, and the attenuation pattern corresponds to the spatially varying attenuation properties of the attenuation leaf.

In accordance with an embodiment of the present invention the attenuation pattern includes a region of substantial attenuation shaped according to a shape of the corresponding organ segment, and the positioner is operable to position the region of substantial attenuation between the radiation source and the corresponding organ segment so as to protect the corresponding organ segment from the corresponding beam segment.

In accordance with an embodiment of the present invention the attenuation pattern outside the region of substantial attenuation is bi-laterally monotonically increasing with distance from the leaf center.

In accordance with an embodiment of the present invention the leaves are high-attenuation leaves so as to substantially limit the radiation beam to pass only between the leaves and be collimated between the leaves.

There is also provided In accordance with an embodiment of the present invention a radiotherapy system including a radiation source operable to produce a radiation beam towards a target, an orientation changer operable to change a relative position of the radiation source with respect to the target, and a multileaf attenuator including attenuating leaves including respective spatially varying attenuation properties and a positioner in communication with the orientation changer, each of the attenuating leaves having a leaf length, leaf thickness, leaf center and leaf direction, wherein the leaf direction is a line intersecting the leaf center along the leaf thickness, wherein the radiation beam includes beam segments, wherein a beam segment is the part of the beam intercepted by one of the attenuating leaves, and wherein the target includes target segments, wherein a target segment is that part of the target that intercepts a corresponding one of the beam segments, wherein each of the attenuating leaves is operative to modulate an intensity of a corresponding beam segment by selective attenuation of the leaf thickness along the leaf length, and wherein the positioner is operable to vary at least one of a leaf center position and a leaf direction relative to the radiation source in accordance with positions of the corresponding target segment and the radiation source.

In accordance with an embodiment of the present invention the radiotherapy system further includes a beam shaper operable to collimate the radiation beam according to a shape of the target.

It is noted that the invention also includes moving the multiple attenuating leaves relative to the source and relative to themselves while no orientation is changing, and/or prior to beam turn-on.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1A:
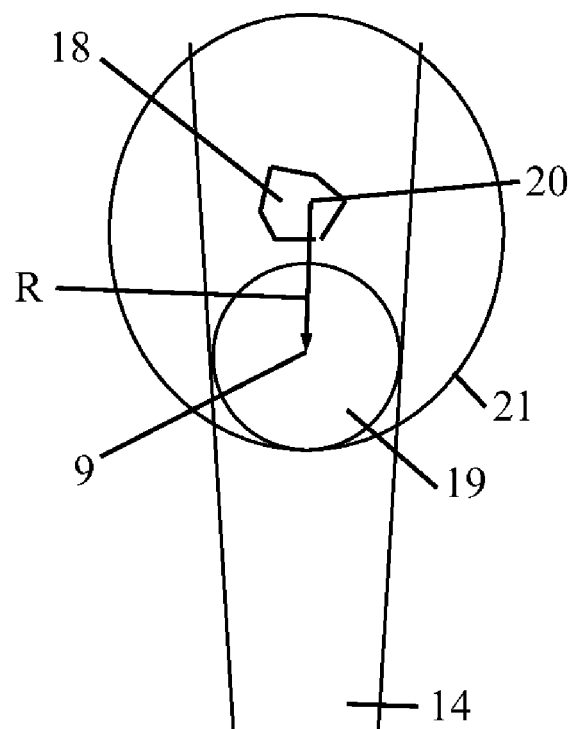
FIG. 1A is a simplified illustration of a stereotactic radiotherapy system with a rotating attenuator, constructed and operative in accordance with an embodiment of the present invention.
Figure 1A:
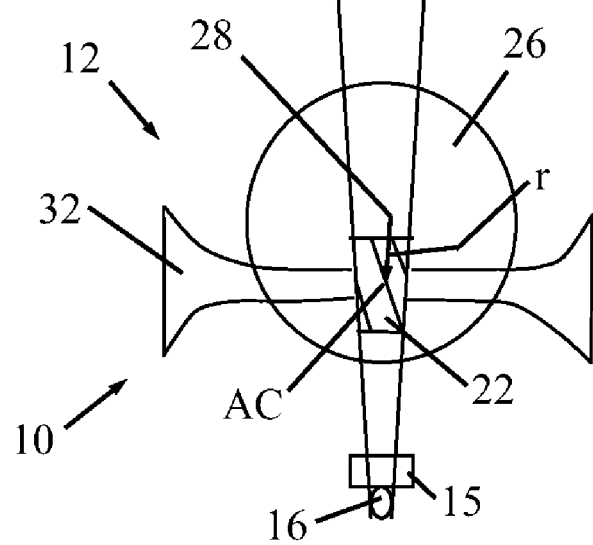

Reference is now made to FIG. 1A, which illustrates a schematic view of a stereotactic radiotherapy system 10 with a rotating attenuator 12, constructed and operative in accordance with an embodiment of the present invention.

System 10 is illustrated and described as an isocentric radiotherapy system, wherein a radiation beam 14 emitted by a radiation source 16 is oriented toward a target 18 from a discrete or continuous set of orientations. (Radiation source 16 may be any suitable radiation source, such as but not limited to, a cobalt source, LINAC, etc.) Isocentricity refers to rotation of the radiation source 16 and/or the target 18 about a target rotational axis 20 typically intersecting the target (perpendicular to the drawing sheet). In such a system, the target 18 and an organ 19 are rotated about the target rotational axis 20, relative to radiation beam 14, whereas the length of the organ rotational radius R equals the distance of the organ center 9 from the target rotational axis 20. A turntable 21 may be used to rotate target 18 and organ 19 (e.g., an upright or reclining patient support turntable). In FIG. 1A, radiation source 16 is stationary, whereas target 18 and organ 19 rotate about target rotational axis 20. However, the invention is not limited to stationary source systems System 10 includes a radiation attenuator 22 placed between source 16 and target 18. Attenuator 22 may be constructed of any suitable radiation attenuating material, such as but not limited to, lead, brass, tungsten, uranium, etc. Attenuator 22 has an attenuator center AC. It is desired to attenuate the radiation impinging upon the organ 19.

As mentioned before, target 18 and organ 19 rotate about target rotational axis 20. Turntable 21 forms an orientation changer operable to change a relative position of the radiation source 16 with respect to the target 18. Attenuator 22 is arranged to rotate about a positioner rotational axis 28 with a positioner rotational radius r, determined by the distance of the attenuator center AC to the rotational axis 28, in synchrony with the organ rotation. Synchronized rotation means that the two objects rotate with the same rotational speed about parallel rotational axes with respective parallel lines intersecting respectively the objects' centers and the rotational axes. Rotator 26 (also referred to as a turntable or positioner 26) rotates the attenuator. Rotator 26 may be any suitable motor, encoder, actuator, etc.

In FIG. 1A, a radiation beam 14 is attenuated by attenuator 22 such that organ 19 receives a much lower dose of radiation. Any portion of the radiation beam 14 to the sides of attenuator 22 may reach organ 19. When a vector (in this case the beam originating at the origin 16) follows a path in space, the scaled version of the vector follows a scaled path. In the illustrated embodiment, the path is a circle (the trajectory of the center of organ 19) having a rotational radius R about a center (axis 20), and the scaled path is a scaled circular trajectory (that of the center of the attenuator 22) having a scaled rotational radius r parallel to R. Consequently, the beam 14 oriented towards organ 19 whose location is represented by a vector originating at radiation source 16 can be attenuated by attenuator 22 located near the tip of the scaled vector such that the scaling factor is smaller than one. The attenuator material and thickness along the vector determine the attenuation properties.

System 10 may also include a beam shaper 15 (e.g., a MLC) operable to collimate the radiation beam 14 according to a shape of the target 18.

Figure 1B:
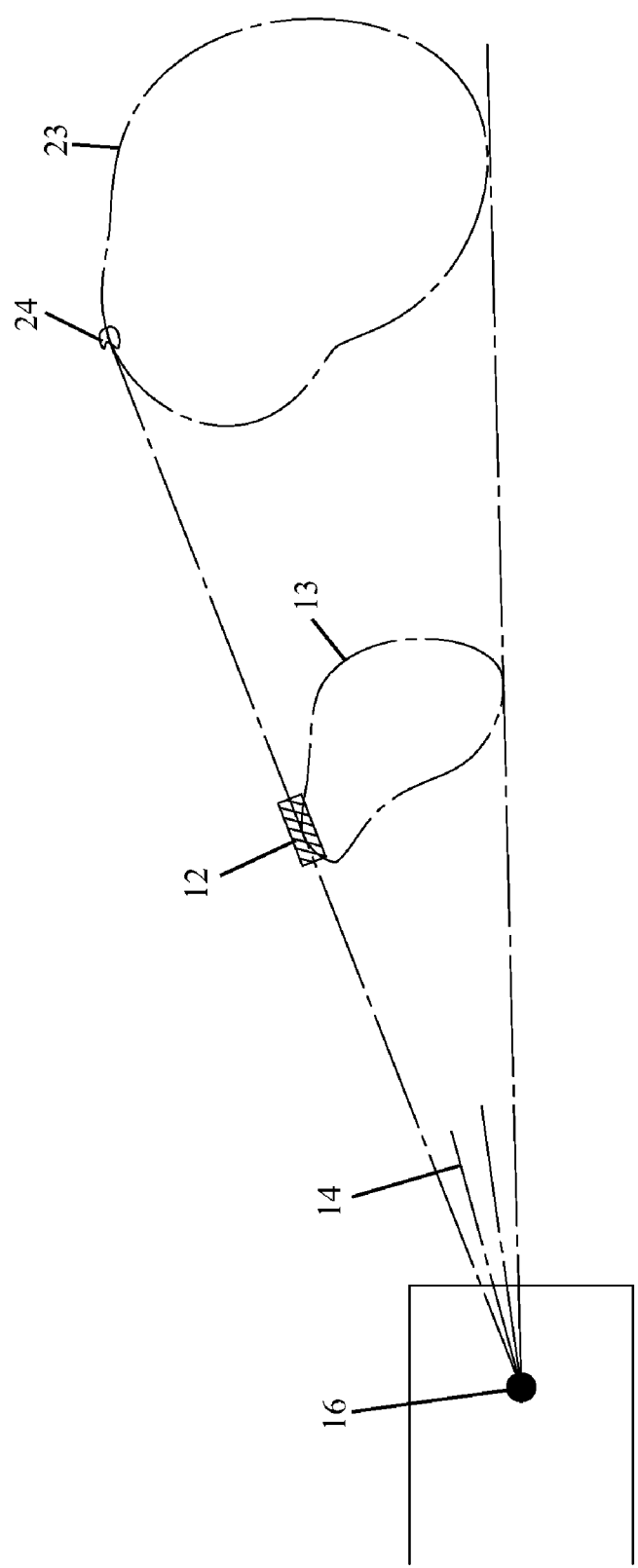
FIG. 1B is a simplified illustration of trajectories for an attenuator and object (organ) in the stereotactic radiotherapy system of an embodiment of the invention.

Reference is now made to FIG. 1B, which illustrates a schematic view of a stereotactic radiotherapy system 10 with an attenuator 12 constructed and operative in accordance with an embodiment of the present invention. The invention makes use of the following geometrical observation: when a radius vector (originating at an origin, in this case, beam 14 originating at radiation source 16) follows a trajectory in space, the scaled version of the radius vector follows a scaled trajectory.

In FIG. 1B, the trajectory 13 of attenuator 12 is the scaled trajectory of the planar trajectory 23 of an organ 24. As an example, when the trajectory is a circle having a rotational radius about a first rotational axis, then the scaled trajectory is a scaled circle having a scaled rotational radius about a second rotational axis parallel to the first one Consequently, a beam oriented toward an object whose location is represented by a radius vector originating at a radiation source can be attenuated by an attenuator whose location is represented by a scaled vector such that the scaling factor is smaller than one. The attenuator thickness along the radius vector and the attenuator material determine the attenuation properties.

Figure 1C:
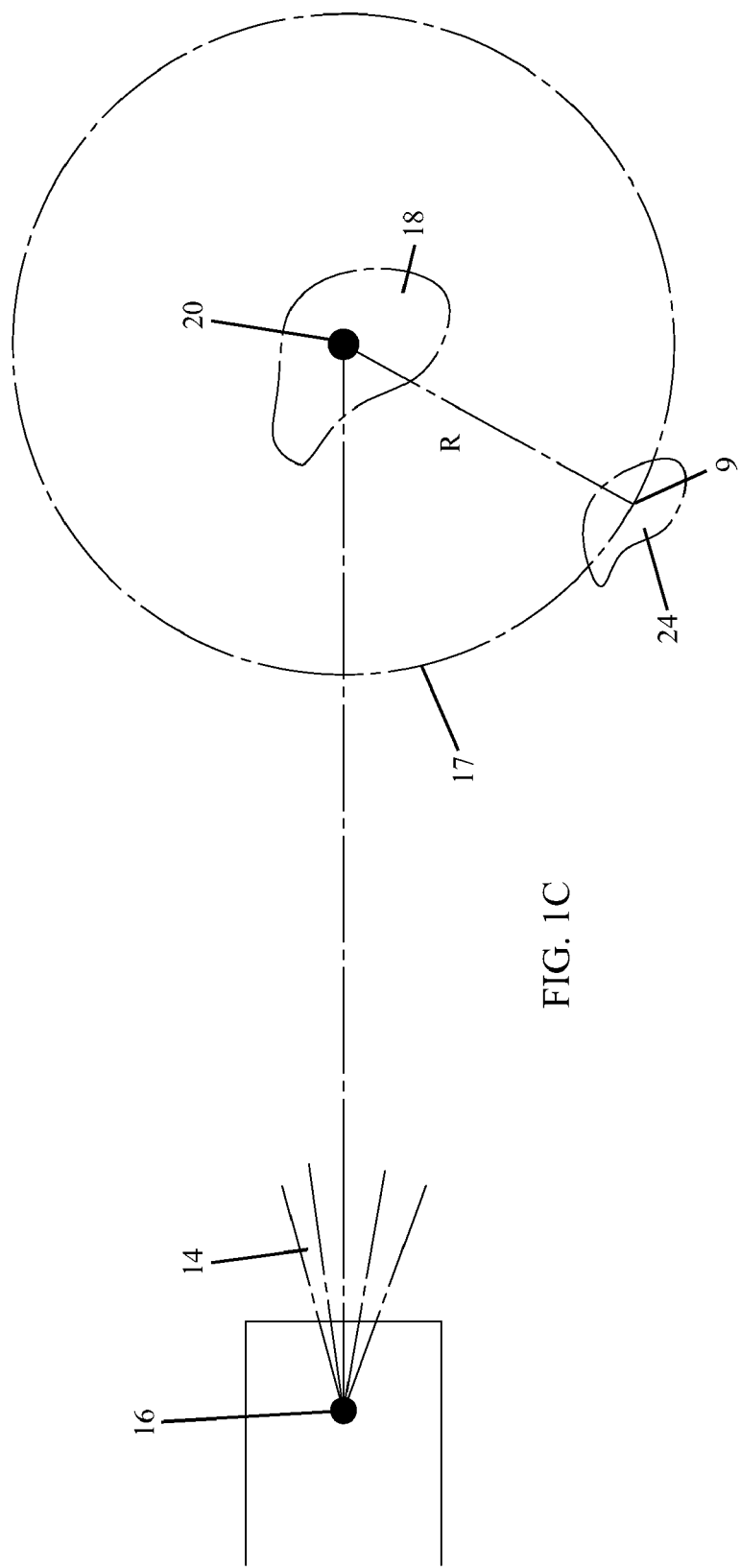
FIG. 1C is a simplified illustration of a cross-section of an isocentric system with a stationary radiation source, wherein a target and organ rotate about a target rotational axis, in accordance with an embodiment of the present invention.
Figure 2A:
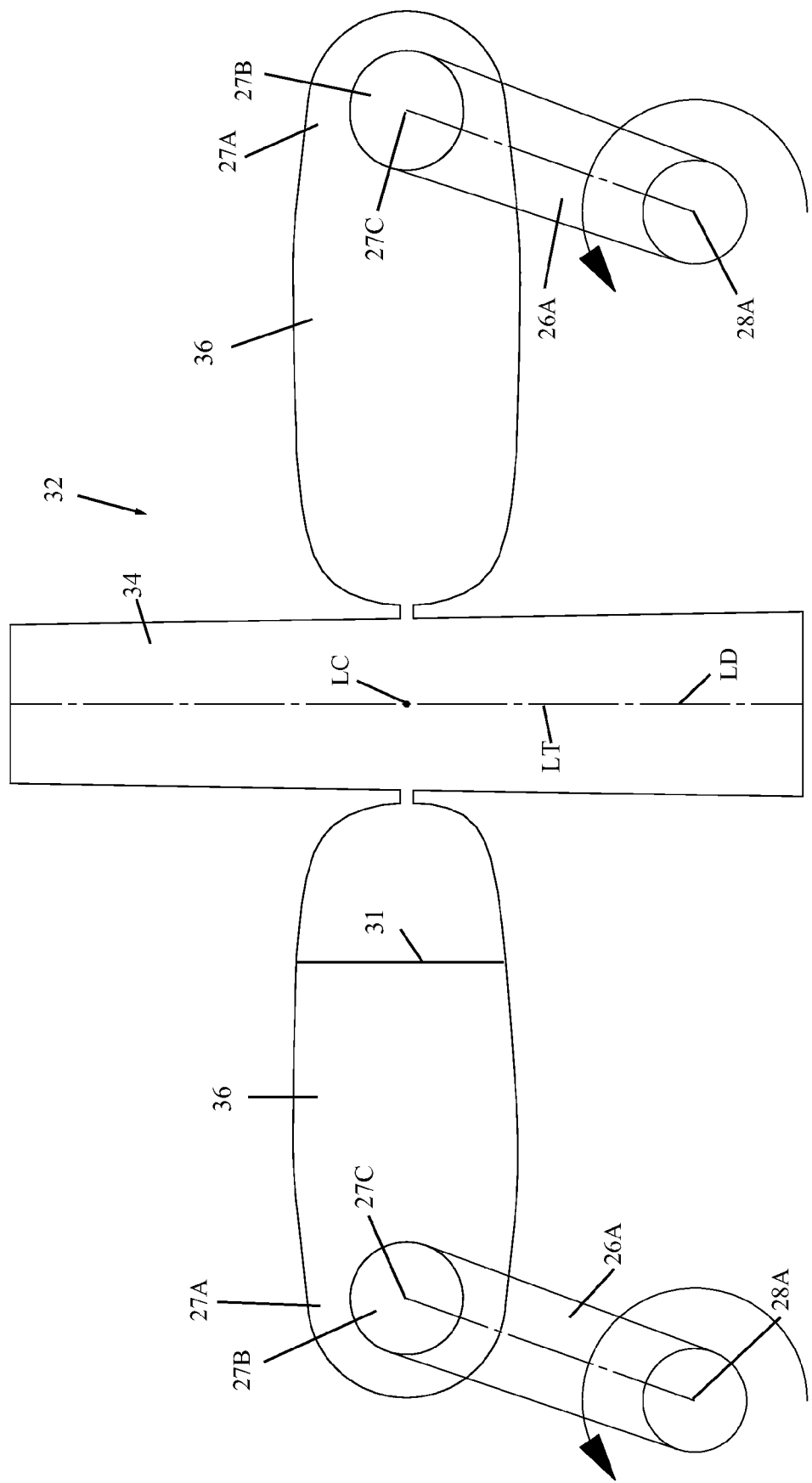
FIG. 2A is a simplified illustration of an attenuator leaf, constructed and operative in accordance with an embodiment of the present invention.
Figure 3A:
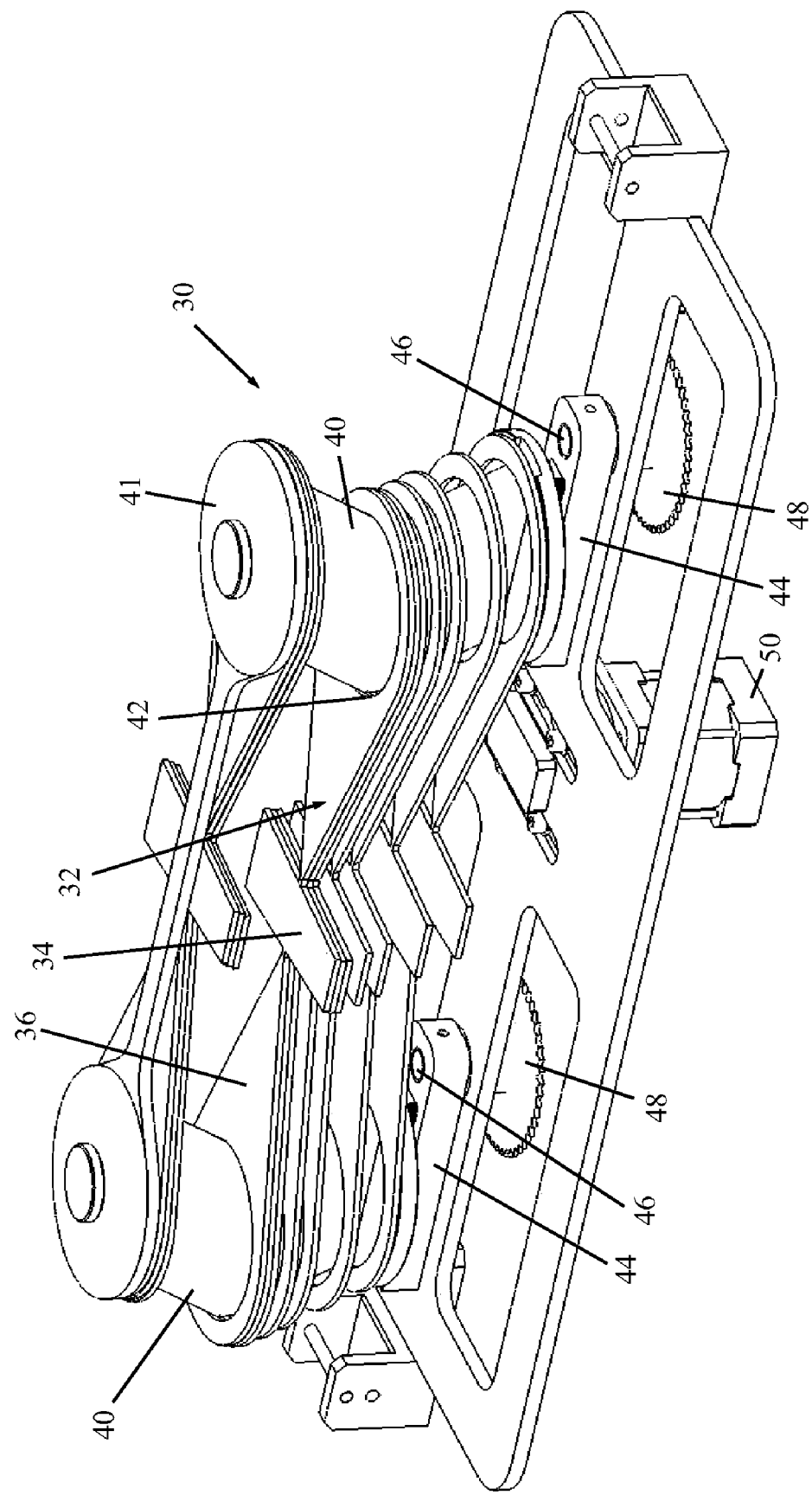
FIGS. 3A-3D are simplified illustrations of a multileaf attenuator (MLA), constructed and operative in accordance with an embodiment of the present invention, with the leaves at different rotational positions.
Figure 3B:
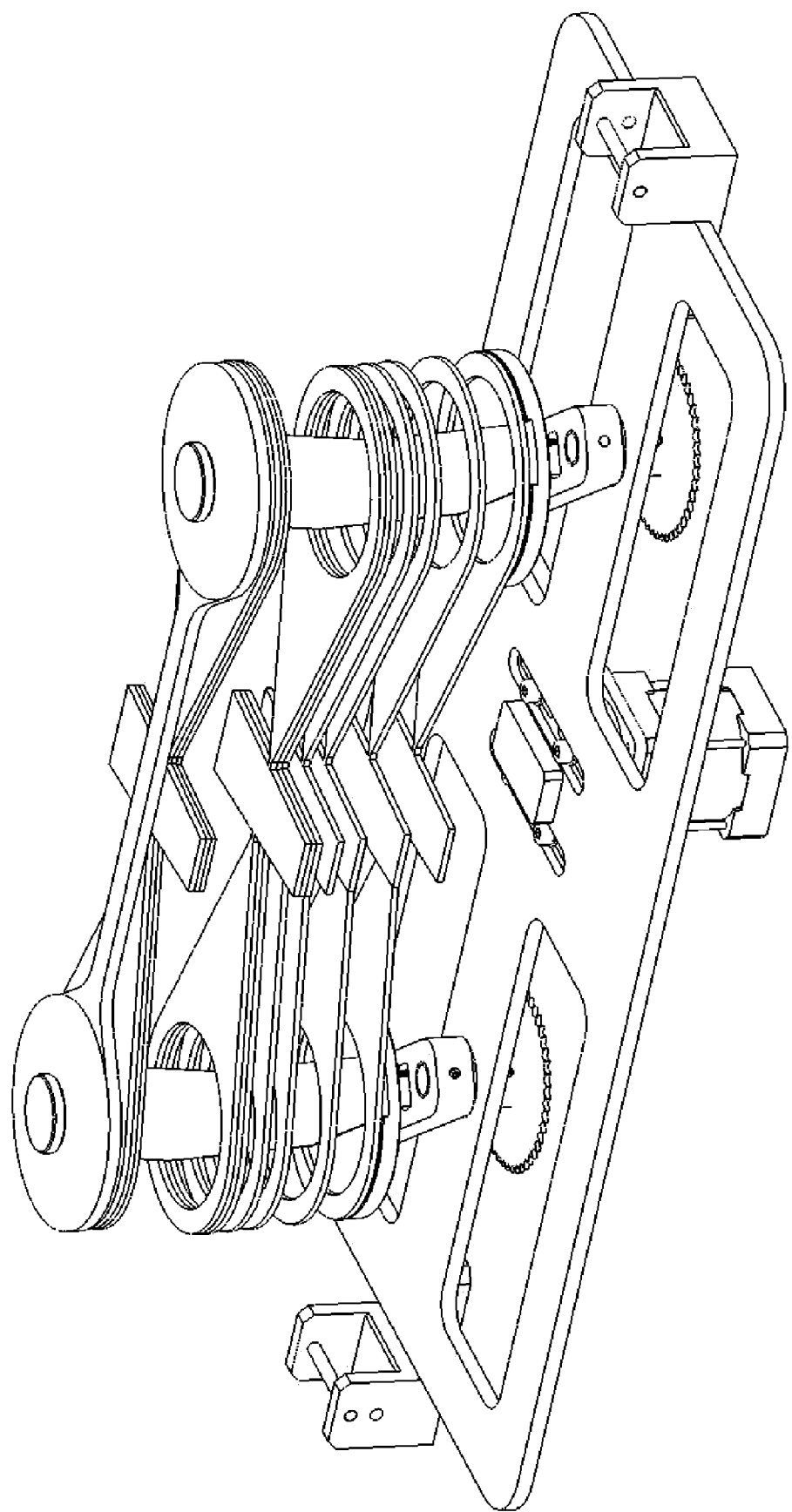
Figure 3C:
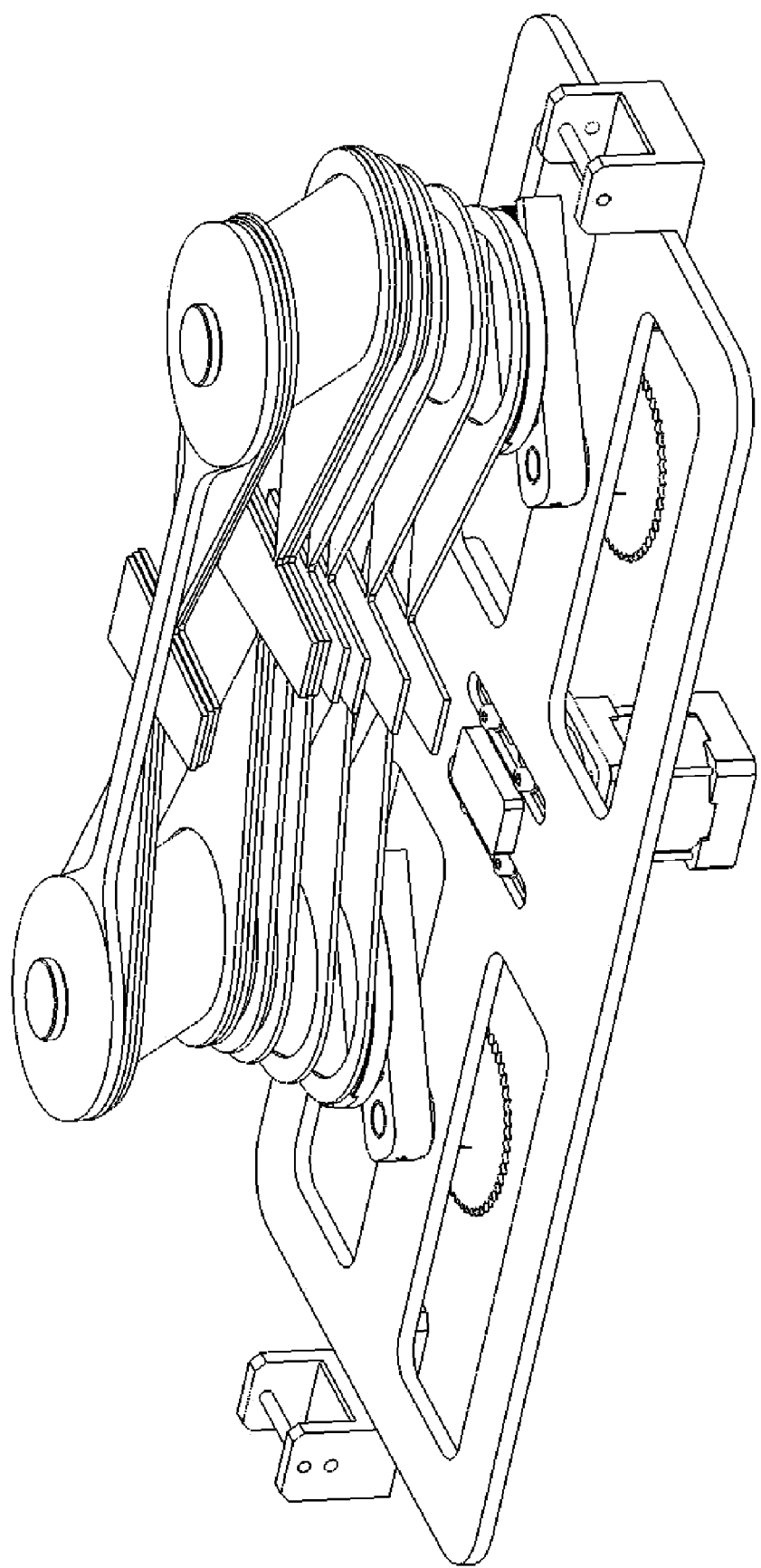
Figure 3D:
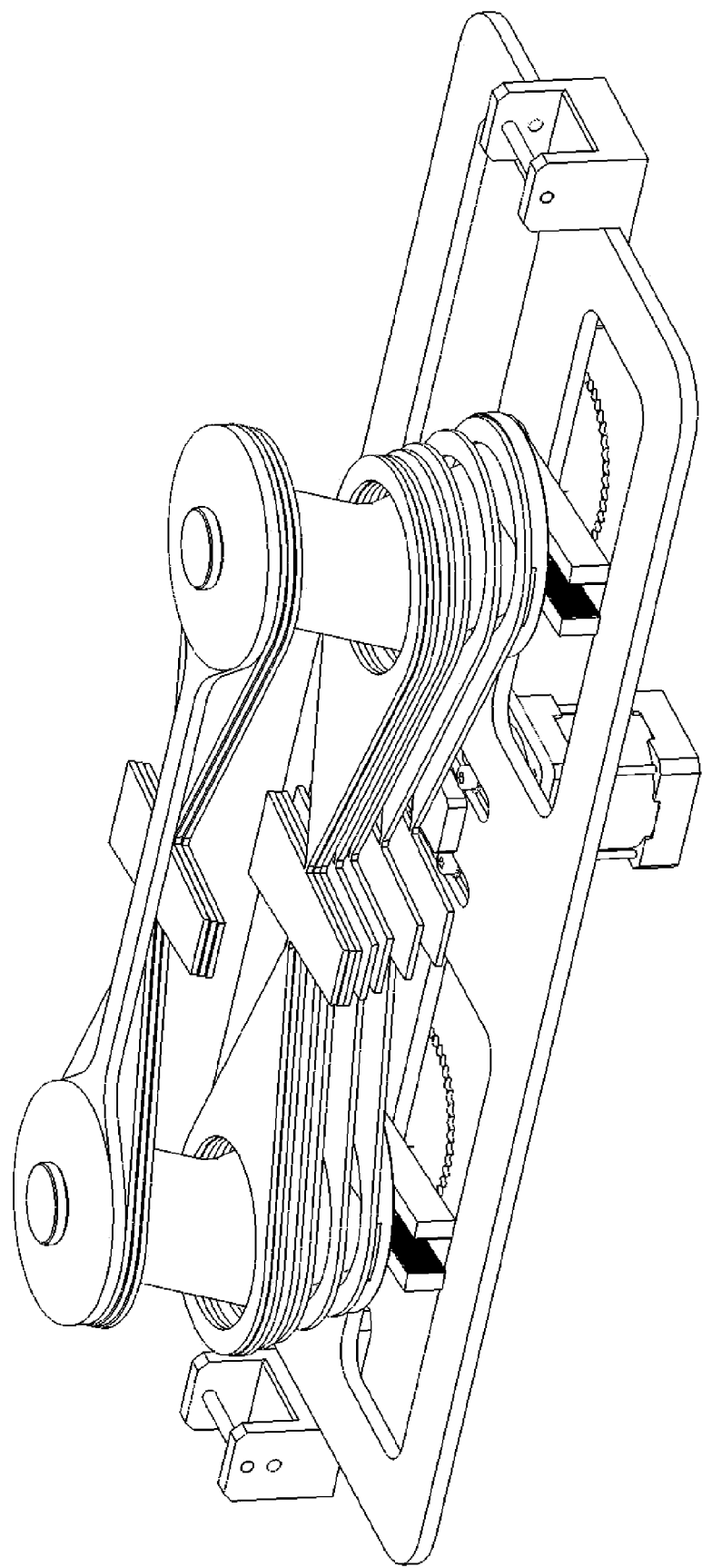

FIG. 1C illustrates a schematic view of a cross section of an isocentric stereotactic radiotherapy system with an attenuator (not shown, but can be any of the attenuators of the invention) constructed and operative in accordance with an embodiment of the present invention. The system incorporates a stationary source 16, wherein target 18 and organ 24 rotate about target rotational axis 20. Isocentricity amounts to rotation of the radiation source 16 and/or the target 18 about target rotational axis 20 typically intersecting the target 18. In such a system, organ rotation about the target rotational axis 20 along organ trajectory 17, relative to radiation beam 14, has a rotational radius R defined by the distance of the organ center 9 from the target rotational axis 20. As mentioned before, the invention is not limited to isocentric systems. In accordance with an embodiment of the present invention, the attenuator is not just the simple attenuator shown in FIG. 1A, but instead includes a multileaf attenuator (MLA) 30, as shown in FIG. 3A. FIG. 2A illustrates an example of just one attenuating leaf 32 of MLA 30, but as will be described further below with reference to FIGS. 3A-3D, MLA 30 preferably includes a multiplicity of attenuating leaves. (FIG. 1A shows an attenuating leaf 32 as well).

It is noted that an attenuating leaf differs from a collimating leaf, i.e., one used in a multi-leaf collimator (MLC), in that the MLC leaf is configured to reduce beam intensity to a (constant) low-level, whereas the MLA leaf is configured to allow substantial (multi-valued) intensity levels.

The MLA leaf has a length, height and thickness, as well as a center and a direction. The leaf thickness and the leaf material determine the attenuation for a given beam energy. The MLA height determines the heights of the corresponding segments of the beam, the target and the organ respectively. Modulating the intensity of a beam segment by a corresponding MLA leaf may be according to a generally one-dimensional attenuation pattern of the leaf thickness and/or the leaf material along the leaf length. A leaf direction is a line intersecting the leaf center along the leaf thickness. For example, the attenuating leaf 32 in FIG. 2A has a central attenuating portion 34 of large thickness, with two wing projections 36 that protrude to the sides of central attenuating portion 34. The attenuating portion 34 is constructed to substantially attenuate a part of a beam segment while the two wing projections are constructed to modulate the other part of the beam segment. The leaf direction LD is a line intersecting the leaf center LC along the leaf thickness LT. The wing projections 36 are very thin at the junction with central attenuating portion 34 and gradually get thicker towards the ends of the effective portion 31 of leaf 32, i.e., the attenuation associated with the wing projections is monotonically increasing with distance from the central attenuating portion 34.

In FIG. 2A, a positioner 26A is rotatably coupled to leaf portions 27A by means of a rotational coupler 27B having a coupler center 27C. Positioner 26A is operable to position any of the attenuating leaves 32 by positioning the two leaf portions 27A. For example, when positioner 26A rotates about positioner rotational axes 28A, the leaf center LC follows a circular trajectory with a leaf rotational radius determined by the distance between the positioner rotational axis 28A and the corresponding coupler center 27C. Throughout such a rotation the leaf direction LT stays parallel to its initial direction.

Figure 2B:
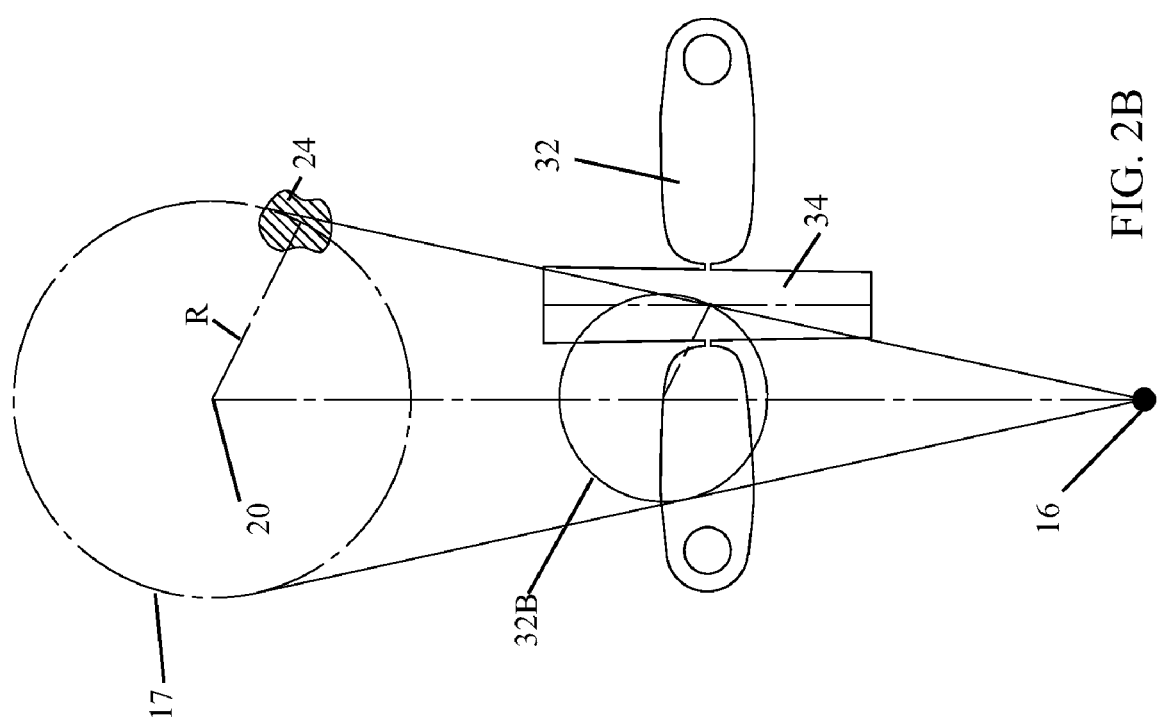
FIG. 2B is a simplified illustration of a radiation source, leaf, trajectory of the leaf center, organ, target rotational axis, organ rotational radius and organ trajectory, in accordance with an embodiment of the present invention.

Reference is now made additionally to FIG. 2B, which illustrates radiation source 16, leaf 32, leaf center trajectory 32B of the leaf center, organ 24, target rotational axis 20, organ rotational radius R and organ trajectory 17. The attenuation pattern of the leaf 32 is obtained by variation of the leaf material and/or the leaf thickness along the leaf length. An attenuation pattern may include a region of substantial attenuation 34 acting as a shielding region. Positioner 26A (FIG. 2A) has positioner rotational axes 28A (FIG. 2A) parallel to the target rotational axis 20 (shown in FIG. 2B). Positioner 26A can position the leaf portions on respective common-radius circular trajectories about respective positioner rotational axes 28A parallel to the target rotational axis 20.

An organ segment may be protected by properly positioning the corresponding shielding region between the radiation source and the organ segment. In the exemplary isocentric system, organ 24 rotates about the target rotational axis 20, the positioner 26A synchronously rotates the shielding region about positioner rotational axis 28A parallel to the target rotational axis 20. Synchronous rotation of two objects about respective parallel rotational axes means that the respective vectors defining the objects locations relative to the respective rotational axes are parallel and in the same direction. The shielding region rotational radius and the distance of the positioner rotational axis from the radiation source relate respectively to the organ rotational radius and the distance of the target rotational axis from the radiation source by a scaling factor.

In the example of FIG. 2A, in order to protect segments of organ 24, the leaf center LC of the leaf 32 is between the radiation source and the center of the organ segment, and the leaf direction LD is directed generally toward the center of the organ segment. The direction may be maintained during the synchronized rotation of the leaf 32 by, for example, further rotating the leaf end-points respectively about the leaf center. When the rotational radius of the organ segment is very small compared to the distance of the rotational axis from the radiation source, the leaf direction during rotation may be kept parallel to the line intersecting the radiation source and the target rotational axis, as illustrated in FIG. 2B. Such a motion may be accomplished by synchronously rotating leaf portions about respective positioner rotational axes parallel to the target rotational axis, such that the leaf center is between the radiation source and the corresponding organ segment center.

Leaf 32 may incorporate a region of substantially negligible attenuation, such as noted previously where the wing projections 36 are very thin at the junction with central attenuating portion 34. Such a region may be used to provide mechanical support for another leaf region so as to enable efficient positioning of the other leaf region. The attenuating leaf of the present invention may include regions of no attenuation, such as a leaf constructed of disconnected leaf parts that permit radiation to pass without attenuation between adjacent leaf parts, wherein the leaf parts move simultaneously as a rigid body, and the length, center etc, are defined with respect to the collection of the leaf parts, i.e., to the composite leaf. Separate leaves of the present invention may correspond to the same beam segment, and do not necessarily move as a rigid body.

Reference is now made to FIGS. 3A-3D, which illustrate multileaf attenuator (MLA) 30, constructed and operative in accordance with an embodiment of the present invention.

Figure 3E:
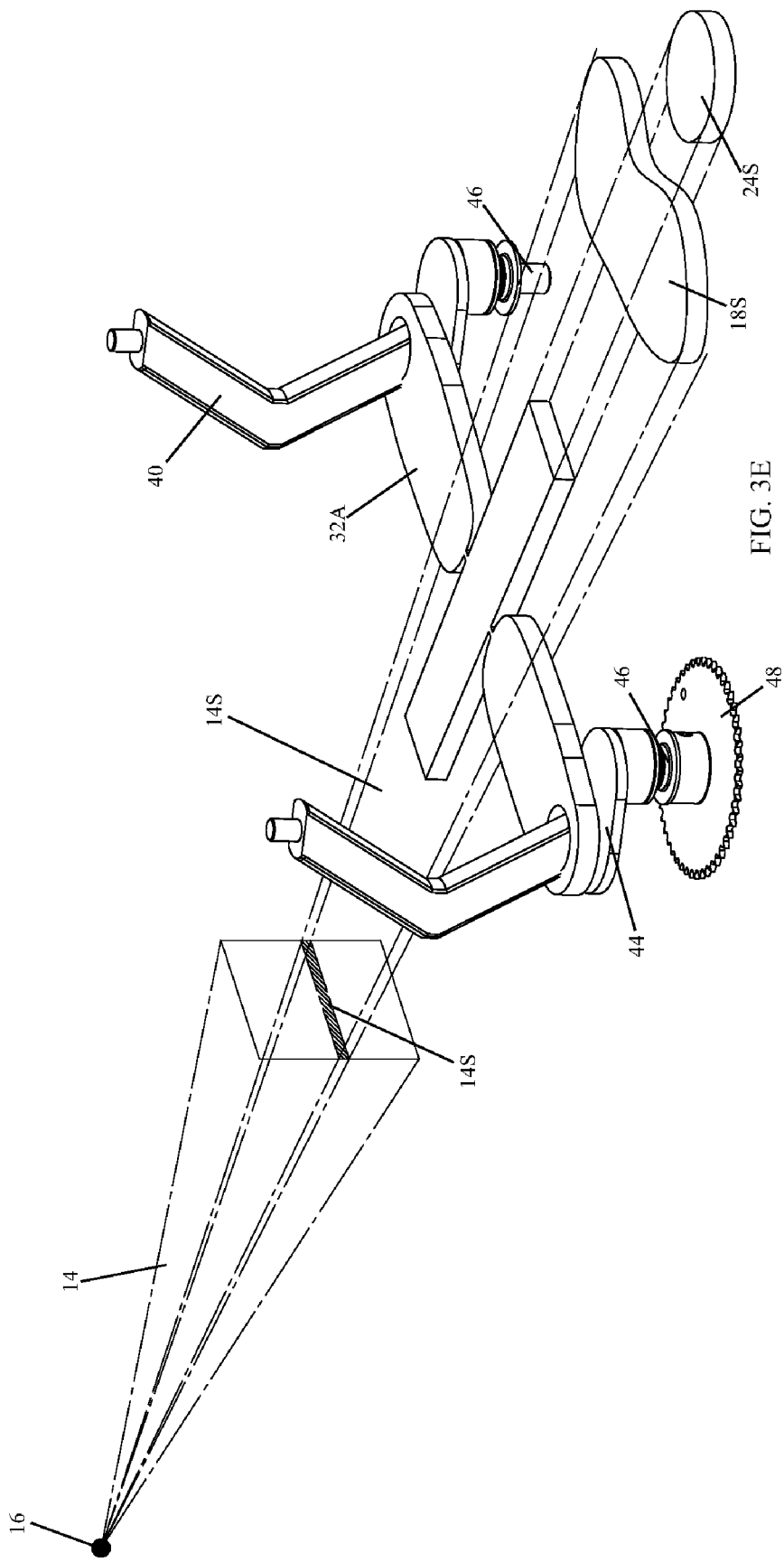
FIG. 3E is a simplified illustration of a multileaf attenuator (MLA), constructed and operative in accordance with another embodiment of the present invention.

MLA 30 includes a multiplicity of attenuating leaves 32, described previously with reference to FIG. 2A. Attenuating leaves 32 are configured to selectively attenuate beam intensity. The beam is attenuated according to respective multi-valued attenuation patterns along the respective leaves' lengths. A leaf may be positioned according to the corresponding organ segment such that a thick portion of the leaf, acting as a shield, is between the radiation source and the organ segment. Since different organ segments may rotate about the target rotational axis with different rotational radii, the respectively corresponding leaves may follow. Rotating the leaves about a common rotational axis but with different rotational radii may be accomplished by rotatingly coupling the leaves 32 to a template 40 or pair of templates 40 (also referred to as positioner templates). The templates are shaped so as to provide the required rotational radii for the leaves when the templates rotate about respective positioner rotational axes parallel to the target rotational axis, as illustrated in FIG. 3E.

Since organ segments may have different shapes as well, the shields of the respectively corresponding leaves may be shaped accordingly. For example, when an organ segment is to be protected from all beam orientations, the corresponding shield should be at least as long (along the leaf length) as the longest dimension of the corresponding organ segment, scaled by the ratio of distances from the radiation source of the leaf center and the center of the organ segment. In such a case, such a shield protects a circle inscribing the corresponding organ segment, as illustrated in FIG. 3E. Referring to FIG. 3A, the leaves 32 are thus stacked along templates 40 and are secured at the top of the template 40 with a cover 41. The base of each template 40 may be mounted on a rotation arm 44 which rotates about a spindle 46 (also referred to as positioner rotational axis 46) of a gear 48. Gears 48 may be connected (by belts or gear trains) to a motor 50. Thus, turning of gears 48 rotates rotation arms 44 about their spindles 46 and causes the templates 40 and attenuating leaves 32 to rotate about spindles 46.

FIGS. 3A-3D illustrate progressive clockwise (as viewed from above) rotation of MLA 30, respectively at west, northwest, northeast and south positions.

Irradiation reduction of a target segment by the shield of a corresponding leaf designed to protect an organ may be inversely proportional to the distance from the protected organ. In order to increase homogeneity of accumulated target dose, the attenuating pattern of a leaf may compensate by reducing beam intensity (i.e., increasing leaf thickness) away from the shield in a way exemplified by the intensity profile described by Brahme (although the invention is not limited to this profile).

Prior to rotation, the leaves end-points may be initially positioned relative to each other according to the organ shape, and relative to the positioner rotational axis according to the rotational radii of the respective organ segments.

Phrased in another way, MLA 30 has attenuating leaves 32 that include respective spatially varying attenuation properties. Positioner 26 is in communication with the turntable 21 of the orientation changer. The radiation beam includes one or more beam segments (FIG. 3E shows one beam segment). The beam segment is the part of the beam intercepted by one of the attenuating leaves. The target 18 includes one or more target segments (again FIG. 3E shows a beam segment 14S, a target segment 18S and an organ segment 24S). The target segment is that part of the target that intercepts a corresponding one of the beam segments. Each of the attenuating leaves is operative to modulate an intensity of a corresponding beam segment by selective attenuation of the leaf thickness along the leaf length. Positioner 26 is operable to vary at least one of a leaf center position and a leaf direction relative to the radiation source 16 in accordance with positions of the corresponding target segment and the radiation source 16.

In the embodiment of FIGS. 3A-3D, the respective leaves' rotational radii is determined with a fabricated template corresponding to the organ.

Figure 4:
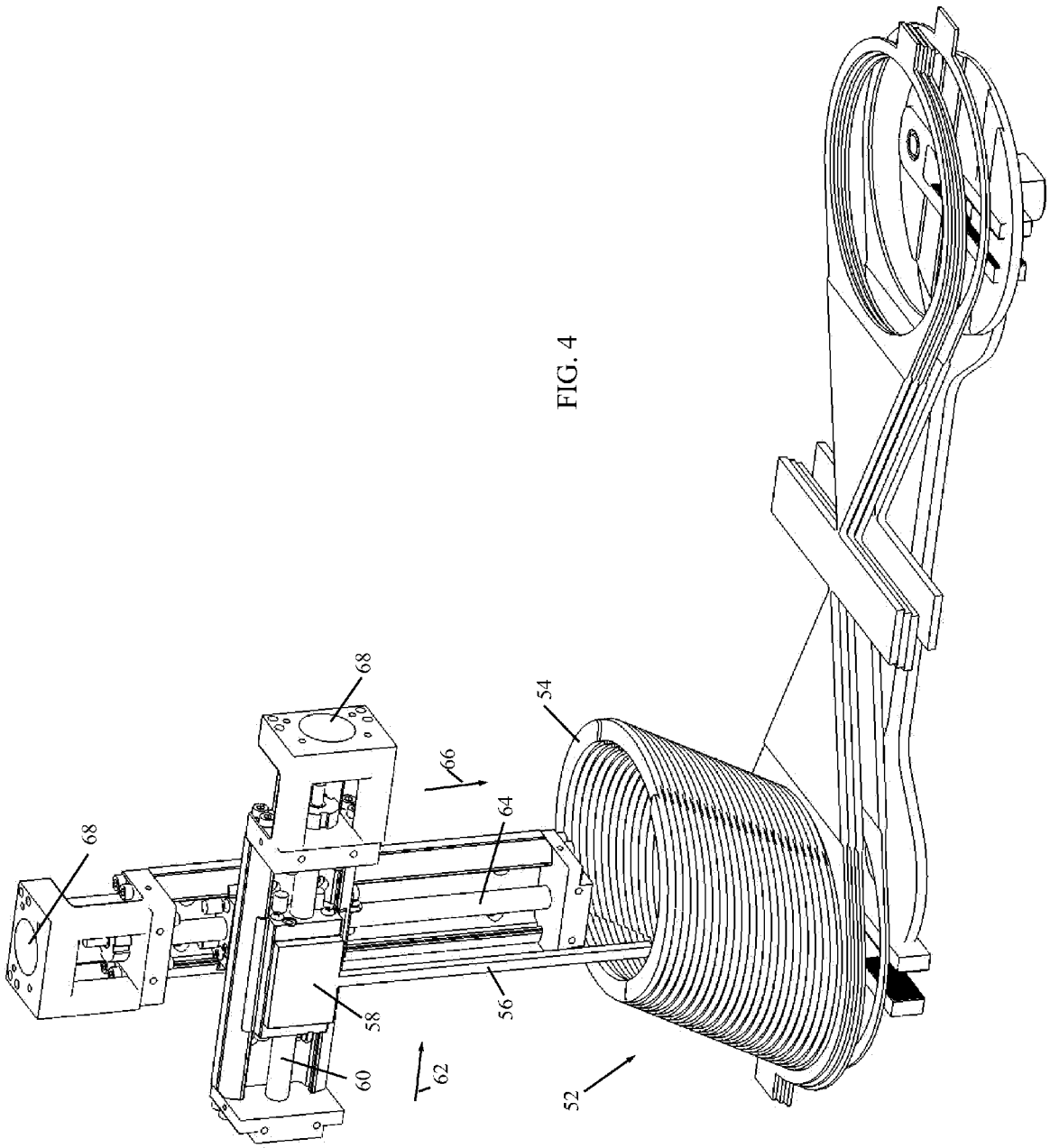
FIG. 4 is a simplified illustration of a multileaf attenuator (MLA), constructed and operative in accordance with yet another embodiment of the present invention.

Reference is now made to FIG. 4, which illustrates a multileaf attenuator (MLA), constructed and operative in accordance with another embodiment of the present invention. In this embodiment, the template 52 is made of template segments whose relative positions are fashioned robotically, wherein the data related to the shape and rotational radius of the organ is provided by a treatment plan.

In the illustrated embodiment, the template 52 includes a plurality of template segments 54, such as rings, stacked one on top of another. A robot arm 56 extends from a base 58, which is slidingly mounted on a first track 60 to move along a first axis 62. First track 60 is in turn slidingly mounted on a second track 64 to move along a second axis 66, which may be orthogonal to first axis 62. The sliding motion may be accomplished by mounting on a lead screw, ball screw or machine slide and the like, powered by a motor 68. Moving the arm along axis 66 may select a template segment to be positioned and then moving the arm along axis 62 may position the selected template segment. An additional sliding stage (not shown) may be used to move the selected template segment also in a direction orthogonal to axis 62 and axis 66. The arrangement of the tracks and motors can position robot arm 56 in any x-y-z position to move the segments 54 individually to any position to from the template 52. After reaching the final positions, the segments 54 may be secured together by any means, such as but not limited to, mechanical fasteners, adhesive, etc.

In accordance with another embodiment of the invention, the invention may be used not only for novel attenuation of the radiation beam, but may also be used to rotate multileaf collimator (MLC) leaves for collimating the radiation beam in a novel manner, as is now explained.

It is noted that a conventional MLC uses a pair of high-attenuation opposing leaves to block radiation outside a target segment. The respective positions of the leaves are adjusted according to the projected position of the target segment.

In accordance with an embodiment of the invention, for each target segment, one or more pairs of high-attenuation collimating leaves (like MLC leaves) are operable to rotate parallel to themselves with rotational radii about respective positioner rotational axes parallel to a target rotational axis with asynchronous rotation, e.g., they may rotate in different directions. As similarly described for the attenuating leaves, in this embodiment that uses the leaves for collimation; the inter-leaf spacing depends on the respective rotational angles. Such angles may be selected so as to match the inter-leaf spacing to the target segment length. When the target rotates or moves, the length and/or position of each projected target segment may change. As similarly described for the attenuating leaves, the positioner in communication with the orientation changer may adjust the rotational angles so that the inter-leaf spacing matches the projected target segment.

In contradistinction to prior art MLC, the present invention enables rotating the leaves using the same two rotational angles for the multiplicity of leaves in corresponding segments, whereas the multiplicity of leaves may have different rotational radii. Furthermore, in the present invention, the positioner can move the MLC leaves perpendicular to the beam and additionally along the beam direction as well. In particular, the centers of the defining edges of the leaves may be rotated with respective rotational radii about respective rotational axes perpendicular to the beam. In such a case, a beam segment is collimated on two sides (e.g., left and right) by corresponding two leaves according to the respective rotational radii, the respective rotational axes locations, and the respective rotational angles. The leaves may or may not be moved parallel to themselves. The leaves may be rotated simultaneously; for example, the right bank of leaves and the left bank are respectively rotated by one motor each (i.e., one positioner rotational axis each) for the whole bank (instead of driving each leaf with an individual motor like in the prior art). When the target is rotated about a target rotational axis, the positioner rotational axes may be parallel to the target rotational axis.

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. A radiotherapy system comprising:
    a radiation source operable to produce a radiation beam towards a target;
    an orientation changer operable to change a relative position of said radiation source with respect to said target; and
    a multileaf attenuator comprising attenuating leaves comprising respective spatially varying attenuation properties and a positioner in communication with the orientation changer, each of said attenuating leaves having a leaf length, leaf thickness, leaf center and leaf direction, wherein the leaf direction is a line intersecting the leaf center along the leaf thickness,
    wherein said radiation beam comprises one or more beam segments, wherein a beam segment is the part of the beam intercepted by one of said attenuating leaves, and wherein said target comprises one or more target segments, wherein a target segment is that part of said target that intercepts a corresponding one of said beam segments, wherein each of said attenuating leaves is operative to modulate an intensity of a corresponding beam segment by selective attenuation of the leaf thickness along the leaf length, and wherein said positioner is operable to vary at least one of a leaf center position and a leaf direction relative to said radiation source in accordance with positions of the corresponding target segment and said radiation source, and wherein the radiation source is stationary, and wherein said orientation changer is operable to rotate said radiation about a rotational axis which is generally vertical, and the radiation beam is generally horizontal.

2. The radiotherapy system according to claim 1, further comprising a beam shaper operable to collimate said radiation beam.

3. The radiotherapy system according to claim 1, wherein said leaves are high-attenuation leaves so as to substantially limit the radiation beam to pass only between said leaves and be collimated between said leaves.

* * * * *